United States Patent [19]

Cohen et al.

[11] Patent Number: 4,914,107
[45] Date of Patent: Apr. 3, 1990

[54] METHOD FOR SELECTIVELY BLOCKING 5-HT$_2$ RECEPTORS

[75] Inventors: Marlene L. Cohen; Mark J. Goldberg; Louis Lemberger, all of Indianapolis, Ind.

[73] Assignee: Eli Lilly and Company, Indianapolis, Ind.

[21] Appl. No.: 297,208

[22] Filed: Jan. 17, 1989

[51] Int. Cl.$^4$ .............................................. A61K 31/44
[52] U.S. Cl. .................................................... 514/288
[58] Field of Search ......................................... 514/288

[56] References Cited

U.S. PATENT DOCUMENTS

| | | | |
|---|---|---|---|
| 3,580,916 | 5/1971 | Garbrecht | 260/285.5 |
| 3,904,634 | 9/1975 | Arcari et al. | 260/285.5 |
| 4,491,664 | 1/1985 | Oppolzer | 546/67 |
| 4,714,704 | 12/1987 | Garbrecht et al. | 514/288 |
| 4,734,501 | 3/1988 | Marzoni | 546/69 |

OTHER PUBLICATIONS

Cohen et al., *J. Pharm. Exp. Therap.* 244, 106–112 (1988).

*Primary Examiner*—Stanley J. Friedman
*Attorney, Agent, or Firm*—William C. Martens; Leroy Whitaker; Joseph A. Jones

[57] ABSTRACT

This invention relates to the use in vivo of 1-isopropyl-dihydrolysergic acid as a 5-HT$_2$ antagonist.

4 Claims, No Drawings

METHOD FOR SELECTIVELY BLOCKING 5-HT$_2$ RECEPTORS

BACKGROUND OF THE INVENTION

Garbrecht et al., U.S. Pat. No.4,714,704, and Cohen et al., U.S. Pat. No. 4,713,384, describe dihydrolysergic acid esters of the following formula

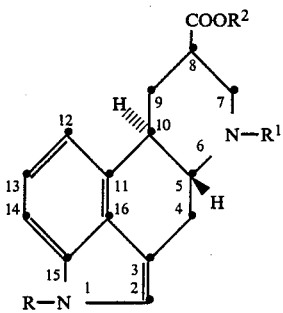

The group R is primary or secondary $C_{1-8}$ alkyl, $CH_2-C_{2-4}$ alkenyl, $C_{3-8}$ cycloalkyl, or $C_{3-6}$ cycloalkyl substituted $C_{1-5}$ primary or secondary alkyl, the total number of carbon atoms not exceeding 8, and the group $R^1$ is $C_1-C_4$ straight chain alkyl.

In Garbrecht et al., the group $R^2$ is $C_{1-3}$ alkyloxy $C_{5-7}$ cycloalkyl, whereas, in Cohen et al., it is hydroxy $C_{5-7}$ cycloalkyl. Highly preferred compounds are those in which R is isopropyl and $R^1$ is methyl.

These compounds, all esters, are recognized to possess selective and highly potent antagonist activity at 5HT$_2$ (5HT=serotonin) receptors upon intravenous or oral administration in rats.

Both of the foregoing classes of esters correspondingly demonstrate, as expected, high affinity in vitro for 5HT$_2$ receptors. These properties are to be compared to the in vitro affinity of a corresponding free acid, 1-isopropyldihydrolysergic acid, i.e., in the foregoing formula, R is isopropyl, $R^1$ is methyl, and $R^2$ is hydrogen.

The latter compound is recognized to exhibit a relatively low level of affinity in vitro for 5HT$_2$ receptors. It has been assumed, therefore, that the free acid would not be a likely candidate for use as an antagonist at 5HT$_2$ receptors, and the literature suggests the utility of the free acid compounds solely as intermediates to active compounds. In this regard, see, e.g., the earlier cited Garbrecht et al. and Cohen et al., as well as Garbrecht, U.S. Pat. No. 3,580,916; Rucman, U.S. Pat. No. 4,230,859; and Hofmann et al., U.S. Pat. No. 3,249,617.

Surprisingly, however, we have recently discovered that 1-isopropyldihydrolysergic acid exhibits relatively high potency as a 5HT$_2$ antagonist in vivo irrespective of its relatively low affinity for these receptors when measured in vitro. It is thus to the use of 1-isopropyldihydrolysergic acid as a 5HT$_2$ antagonist, whether administered orally or by injection, that this invention is directed.

SUMMARY OF THE INVENTION

Thus, this invention is directed to a method of blocking 5HT$_2$ receptors which comprises administering to a mammal having an excess of serotonin, whether centrally or peripherally, a 5HT$_2$ blocking dose of a compound of the formula

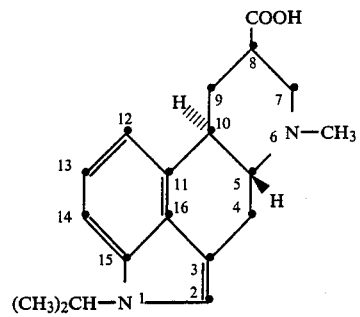

or any of its pharmaceutically acceptable salts.

DETAILED DESCRIPTION OF THE INVENTION

It is recognized that a method whereby 5HT$_2$ receptors are blocked but alpha receptors are not affected by a particular compound at a given dose level is potentially useful in treating disease states in which an excess of circulating serotonin is a major cause. These disease states include hypertension, anorexia nervosa, depression, mania, carcinoid syndrome, migraine, sexual dysfunction, thrombosis, ischemia, and vasospasm. The lack of alpha receptor inhibitory activity indicates that the usual undesirable side effects associated with alpha receptor blockade—postural hypotension, tachycardia, impotence, and increase plasma renin levels—will not occur. This lack of undesirable side effects is in marked contrast to many presently available hypotensive agents, including ketanserin.

The compound may be administered in the form of its pharmaceutically acceptable salts. Pharmaceutically-acceptable acid addition salts include salts derived from non-toxic inorganic acids such as hydrochloric acid, nitric acid, phosphoric acid, sulfuric acid, hydrobromic acid, hydriodic acid, phosphorous acid, and the like, as well as salts derived from non-toxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, and the like. Examples of such pharmaceutically-acceptable salts thus are sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate, and the like.

In addition, salts of pharmaceutically acceptable alkali and alkaline earth metal may be used. These include, for example, sodium, potassium, lithium, calcium, magnesium, and the like.

In carrying out the therapeutic method of this invention, a pharmaceutically acceptable salt of 1-isopropyldihydrolysergic acid may be formed, and the resulting salt then administered orally or parenterally to a mammal, preferably human, having an excess of circulatory serotonin and for whom it is desirable to block 5HT$_2$ receptors to alleviate symptoms such as high blood pressure, migraine, and the like, attributable to excessive serotonin levels. For parenteral administration, a water soluble salt of the compound may be dissolved in an isotonic salt solution and administered, for example, intravenously. For oral administration, a pharmaceutically acceptable salt of the compound may be mixed with standard pharmaceutical excipients such as starch and the mixture loaded into capsules or made into tablets, each containing preferably about 0.001 to about 100 mg of active compound. Dosage levels of from about 0.001 to about 10 mg/kg are effective in blocking 5HT$_2$ receptors. Preferably, an oral dose is administered about 2 to about 4 times per day, providing a daily dosage in the range of about 0.003 to about 10.0 mg/kg per day.

A variety of oral dosage forms, including suspensions, elixirs, tablets, and the like, can also be utilized and are preparable by standard procedures.

The following examples are provided to illustrate the present invention. They are not intended to be limiting upon the scope thereof.

EXAMPLE 1

In Vitro 5HT$_2$ Affinity of 1-Isopropyldihydrolysergic Acid

Male Wistar rats (150–300 g) (Harlan Sprague-Dawley, Inc., Cumberland, IN) were killed by cervical dislocation. Ring preparations of external rat jugular veins were used as detailed in [(Cohen et al., *J. Pharm. and Exper. Therapeutics* 227, 327–332 (1983); Cohen et al., *J. Pharm. and Exper. Therapeutics* 235, 319–323 (1985).]

Tissues were mounted in organ baths containing 10 ml of modified Krebs' solution of the following composition (millimolar concentrations): NaCl, 118.2; KCl, 4.6; CaCl$_2$.2H$_2$O, 1.6; KH$_2$PO$_4$, 1.2; MgSO$_4$, 1.2; dextrose, 10.0; and NaHCO$_3$, 24.8. Tissue bath solutions were maintained at 37° C. and aerated with 95% O$_2$–5% CO$_2$. Isometric contractions were recorded as changes in grams of force on a Beckman Dynograph with Statham UC-3 transducers and microscale accessory attachments. Tissues were allowed to equilibrate at an initial optimum resting force for 1 to 2 hr before exposure to test compound.

After control contractile responses to serotonin were obtained in the jugular vein, vessels were incubated with appropriate concentrations of the test compound for 1 hr. Responses to serotonin were then repeated in the presence of test compound.

Apparent test compound dissociation constants (K$_B$) were determined for each concentration of test compound according to the following equation:

$$K_B = \frac{(B)}{(\text{dose ratio} - 1)}$$

where (B) is the concentration of the test compound and dose ratio is the ED$_{50}$ of the serotonin in the presence of the test compound divided by the control ED$_{50}$. These results were then expressed as the negative logarithm of the K$_B$ (i.e., −log K$_B$). The data were also analyzed according to the procedure of Arunlakshana and Schild, *Brit. J. Pharmacol.* 14, 48–58 (1959) as previously described [Cohen et al., supra (1983)].

Table I following depicts apparent dissociation constants derived from the ability of 1-isopropyldihydrolysergic acid and that of the corresponding 4-methoxycyclohexyl ester to antagonize serotonin-induced contractions in the rat jugular vein. Affinity at 5HT$_2$ receptors for 1-isopropyldihydrolysergic acid was approximately 10$^{-7}$M. Furthermore, this agent was a competitive antagonist at 5HT$_2$ receptors in the jugular vein as indicated by a slope of the Schild plot that did not differ from negative unity. The free acid was a competitive antagonist at 5HT$_2$ receptors, albeit at an affinity approximately 100-fold lower than that of the 4-methoxycyclohexyl ester.

TABLE I

In vitro Affinity at 5HT$_2$ Receptors in the Rat Jugular Vein

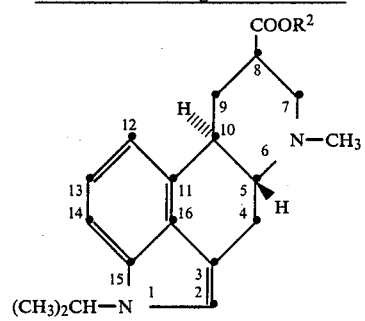

| Compound | R$^2$ | −log K$_B$ ± SE(n)$^a$ | pA$_2$$^b$ | −Slope$^b$ |
|---|---|---|---|---|
| I | 4-methoxy-cyclohexyl | 8.96 ± 0.07 (18) | 9.05 | 0.86 |
| II | H | 7.07 ± 0.11 (12) | 6.82 | 1.29 |
| ratio II/I | | 78 | 170 | |

$^a$Values are means ± S.E. for K$_B$ = [B]/[dose-ratio − 1] where [B] = concentration of antagonist and dose ratio = ED$_{50}$ of the agonist after the antagonist divided by the ED$_{50}$ of the agonist before the antagonist. The number of tissues examined for each antagonist is indicated in parentheses.
$^b$pA$_2$ is the abscissa intercept of the line formed from a Schild plot of log [dose-ratio − ] vs. −log[B] (Arunlakshana and Schild, supra, 1959). Schild plots were constructed from at least two concentrations of the antagonist using the number of tissues indicated in parentheses. The slope of the Schild plots did not differ from unity.

EXAMPLE 2

In Vivo Vascular 5HT$_2$ Blocking Activity of 1-Isopropyldihydrolysergic Acid

Serotonin receptor antagonism was evaluated in pithed Wistar normotensive rats (Charles River, Inc. Portage, MI; 240–374 g) since responses in the pithed preparation are primarily direct vascular effects. Rats were anesthetized with Metofane ® (methoxyflurane), carotid arterial and femoral venous catheters were implanted, and the trachea was cannulated. Rats were pithed and ventilated with room air (Cohen et al., supra, 1983; Cohen et al., supra, 1985). An equilibration period of 15 min. was observed before control measurements and i.v. administration of test compound or vehicle. Increasing intravenous doses of serotonin were injected 15 min. after intravenous administration of test compound or vehicle. As shown in Table II following, administered intravenously, both 1-isopropyldihydrolysergic acid and the corresponding 4-methoxycyclohexyl ester dose-dependently inhibited the pressor response to serotonin in pithed rats. By intravenous administration, 1-isopropyldihydrolysergic acid was only approximately one-third as potent as the ester in blocking vascular 5HT$_2$ receptors.

TABLE II

In Vivo Activity at Vascular (5HT$_2$) Serotonin
Receptors upon Intravenous Administration to Pithed Rats

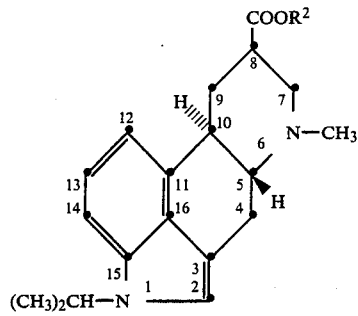

| | Test Compound, Dose (mg/kg iv) | | | | | |
|---|---|---|---|---|---|---|
| | 0 | 0.01 | 0.03 | 0.1 | 0.3 | 1.0 |
| R$^2$ | | | Serotonin ED$_{30}$ (mg/kg iv)$^a$ | | | |
| 4-methoxy-cyclohexyl | 0.03(5) | 0.07 ± 0.02(3) | 0.15 ± 0.03(3) | 1.16 ± 0.51(4) | | |
| H | 0.04(6) | 0.06 ± 0.01(3) | 0.07 ± 0.02(3) | 0.62 ± 0.25(4) | 0.78±0.09(3) | 1.84±0.16(3) |

$^a$Dose of serotonin that produced a 30 mm Hg increase in mean arterial blood pressure.

Since 1-isopropyldihydrolysergic acid required only a three-fold higher intravenous dose than the corresponding 4-methoxycyclohexyl ester to block vascular 5HT$_2$ receptors, a comparison of these compounds with regard to duration of effective blockade of vascular 5HT$_2$ receptors in vivo was conducted.

For these studies pithed rats were treated with vehicle or with the acid or the ester at a dose of 0.1 mg/kg, i.v. and challenged with serotonin (0.1 mg/kg i.v.) at various intervals for 2 hrs. after test compound or vehicle administration. As seen previously, the ester (0.1 mg/kg, i.v.) produced greater inhibition of vascular serotonin receptors than the acid (0.1 mg/kg, i.v.); nevertheless, the acid did produce a marked block of vascular serotonin receptors. Response to serotonin after both the ester and acid administration slowly returned toward saline values although marked inhibition of serotonin vascular response was still apparent 2 hrs. after intravenous administration of either agent. The results are shown in Table III following.

TABLE III

Duration of Inhibition of Vascular (5HT$_2$) Serotonin Receptors
Following Intravenous Administration
of Test Compound to Pithed Rats

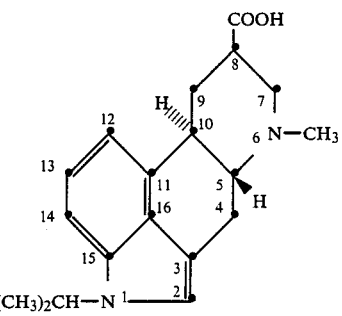

| | | Time (minutes) after Test Compound | | | | |
|---|---|---|---|---|---|---|
| | Dose | 15 | 30 | 60 | 90 | 120 |
| R$^2$ | | Increase in mean blood pressure to serotonin (mm Hg)$^a$ | | | | |
| Control | — | 77 | 82.2 | 82.5 | 85.5 | 82.8 |
| 4-Methoxy-cyclohexyl | 0.1 mg/kg iv | 7.3 | 12.7 | 23.9 | 34.6 | 34.6 |
| H | 0.1 mg/kg iv | 29.7 | 27.8 | 35.3 | 41.7 | 48.1 |
| H | 0.3 mg/kg iv | 3.2 | 3.4 | 4.2 | 9.6 | 13.6 |

$^a$Serotonin was administered intravenously in a dose of 0.1 mg/kg. Points are mean values from 3-4 rats.

We claim:

1. A method of blocking 5HT$_2$ receptors which comprises administering to a mammal having an excess of serotonin, whether centrally or peripherally, a 5HT$_2$ blocking dose of a compound of the formula

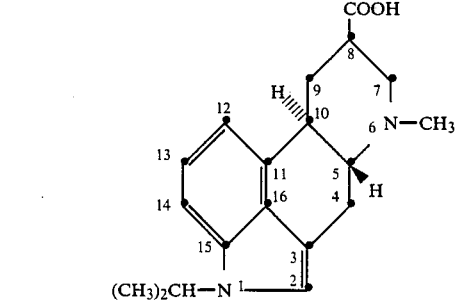

or a pharmaceutically acceptable salt thereof.

2. Method of claim 1, in which the blocking dose is in the range of from about 0.001 to about 100 mg.

3. A method of treating hypertension which comprises administering to a hypertensive mammal a hypotensive dose of a compound of the formula or a pharmaceutically acceptable salt thereof.

4. Method of claim 3, in which the blocking dose is in the range of from about 0.001 mg to about 100 mg.

* * * * *